US010987299B2

(12) United States Patent
Yamamoto et al.

(10) Patent No.: US 10,987,299 B2
(45) Date of Patent: Apr. 27, 2021

(54) POLYLACTIC ACID-CONTAINING AQUEOUS DISPERSION

(71) Applicants: TOYOBO CO., LTD., Osaka (JP); DAITO KASEI KOGYO CO., LTD., Osaka (JP)

(72) Inventors: Shuhei Yamamoto, Tsuruga (JP); Yoshihisa Kasukabe, Osaka (JP); Chikako Yamashita, Tsuruga (JP); Takumi Tanaka, Osaka (JP); Noboru Nagatani, Osaka (JP)

(73) Assignees: TOYOBO CO., LTD., Osaka (JP); DAITO KASEI KOGYO CO., LTD., Osaka (JP)

( * ) Notice: Subject to any disclaimer, the term of this patent is extended or adjusted under 35 U.S.C. 154(b) by 0 days.

(21) Appl. No.: 15/546,586

(22) PCT Filed: Jan. 25, 2016

(86) PCT No.: PCT/JP2016/052027
§ 371 (c)(1),
(2) Date: Jul. 26, 2017

(87) PCT Pub. No.: WO2016/121696
PCT Pub. Date: Aug. 4, 2016

(65) Prior Publication Data
US 2017/0367964 A1  Dec. 28, 2017

(30) Foreign Application Priority Data

Jan. 30, 2015  (JP) .............................. JP2015-016702

(51) Int. Cl.
*A61K 8/85* (2006.01)
*A61K 8/04* (2006.01)
*A61K 8/37* (2006.01)
*A61Q 1/10* (2006.01)
*A61Q 3/02* (2006.01)
*C08L 67/04* (2006.01)
*C08J 3/05* (2006.01)
*C08K 5/10* (2006.01)
*A61K 8/81* (2006.01)
*C08L 101/16* (2006.01)

(52) U.S. Cl.
CPC ............. *A61K 8/85* (2013.01); *A61K 8/04* (2013.01); *A61K 8/37* (2013.01); *A61K 8/81* (2013.01); *A61Q 1/10* (2013.01); *A61Q 3/02* (2013.01); *C08J 3/05* (2013.01); *C08K 5/10* (2013.01); *C08L 67/04* (2013.01); *A61K 2800/52* (2013.01); *C08L 101/16* (2013.01)

(58) Field of Classification Search
CPC ... A61K 8/85; A61K 8/81; A61K 8/04; A61K 8/37; A61K 2800/52; C08L 67/04; C08L 101/16; C08J 3/05; C08K 5/10; A61Q 1/10; A61Q 3/02
See application file for complete search history.

(56) References Cited

U.S. PATENT DOCUMENTS

| 9,901,530 | B2 * | 2/2018 | Doi ......................... A61Q 1/12 |
| 2004/0146540 | A1 * | 7/2004 | Ueda ...................... A61K 8/025 |
| | | | 424/401 |
| 2005/0058712 | A1 * | 3/2005 | Serpelloni ................. C08J 3/05 |
| | | | 424/486 |
| 2005/0228092 | A1 * | 10/2005 | Fujita ...................... C07C 69/40 |
| | | | 524/315 |
| 2011/0274731 | A1 * | 11/2011 | Miyahara ............... A61K 8/064 |
| | | | 424/400 |
| 2013/0309497 | A1 * | 11/2013 | Takezaki ................... C08J 3/14 |
| | | | 428/402 |
| 2013/0316106 | A1 * | 11/2013 | Nakano .................. C08L 67/02 |
| | | | 428/35.5 |

FOREIGN PATENT DOCUMENTS

| CN | 103501755 A | 1/2014 |
| CN | 103509197 A | 1/2014 |
| JP | 2002-097359 A | 4/2002 |
| JP | 2002-121288 A | 4/2002 |
| JP | 2002-356612 A | 12/2002 |
| JP | 2003-277595 A | 10/2003 |
| JP | 2004-099883 A | 4/2004 |
| JP | 2004-107413 A | 4/2004 |
| JP | 2004107413 A * | 4/2004 |

(Continued)

OTHER PUBLICATIONS

JP 2004/107413A in machine translation (Year: 2004).*
Tanford, C., "Physical Chemistry of Macromolecules", pp. 145-147, esp. p. 147, John Wiley & Sons, Inc., publisher (New York) 1961 (Year: 1961).*
Inkinen et al., "From Lactic Acid to Poly(lactic acid) (PLA): Characterization and Analysis of PLA and Its Precursors", Biomacromolecules 12: 523-532 (2011) (Year: 2011).*
Cooper-White et al., "Rheological Properties of Poly(lactides). Effect of Molecular Weight and Temperature of Viscoelasticity of Poly (L-lactic acid)", J Polymer Sci, Part B: Polym Phys 37: 1803-1814 (1999 (Year: 1999).*
Japanese Patent Office, International Search Report in International Patent Application No. PCT/JP2016/052027 (dated Feb. 16, 2016).

*Primary Examiner* — Abigail Vanhorn
(74) *Attorney, Agent, or Firm* — Ledyig, Voit & Mayer, Ltd.

(57) ABSTRACT

Provided is a polylactic-acid-containing aqueous dispersion capable of forming a transparent film at room temperature. A polylactic-acid-containing aqueous dispersion contains (1) polylactic acid; (2) at least one plasticizer selected from the group consisting of dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof; (3) at least one dispersion stabilizer selected from the group consisting of cationic polymers, anionic polymers, polyvinyl alcohols, and non-ionic surfactants; and (4) water.

19 Claims, No Drawings

(56) References Cited

FOREIGN PATENT DOCUMENTS

| | | |
|---|---|---|
| JP | 2004-204219 A | 7/2004 |
| JP | 2006-022242 A | 1/2006 |
| JP | 2006-077186 A | 3/2006 |
| JP | 2006-232975 A | 9/2006 |
| JP | 2006-241400 A | 9/2006 |
| JP | 2007-262119 A | 10/2007 |
| JP | 2008-504404 A | 2/2008 |
| JP | 2011-126798 A | 6/2011 |
| JP | 2011-168552 A | 9/2011 |
| WO | WO 2006/002372 A2 | 1/2006 |
| WO | WO 2012/121704 A1 | 9/2012 |

\* cited by examiner

POLYLACTIC ACID-CONTAINING AQUEOUS DISPERSION

CROSS-REFERENCE TO RELATED APPLICATIONS

This patent application is the U.S. national phase of International Patent Application No. PCT/JP2016/052027, filed on Jan. 25, 2016, which claims the benefit of Japanese Patent Application No. 2015-016702, filed Jan. 30, 2015, the disclosures of which are incorporated herein by reference in their entireties for all purposes.

TECHNICAL FIELD

A polylactic-acid-containing dispersion is disclosed.

BACKGROUND ART

Recent growing awareness of environmental issues has promoted the development of products from biodegradable materials. Polylactic acid, which is formed by polymerizing lactic acid through ester bonds, is known as a biodegradable material. Synthesized from a substance from plants, such as glucose and sucrose, polylactic acid is drawing attention as a carbon-neutral bioplastic and has been in practical use in a range of products, while other applications are now in development.

PTL 1, for example, discloses a polylactic acid that is suitable as a binder for ink and that contains 80 to 100 mol % of a lactic acid residue, wherein the molar ratio (L/D) of L-lactic acid to D-lactic acid is in the range of 1 to 9. PTL 2 discloses an aqueous dispersion suitable for use in, for example, coating, impregnating, spraying, and internal addition for textile products and paper products, obtained by dispersing polylactic acid in water in the presence of a plasticizer and a dispersion stabilizer. PTL 3 discloses a manicure preparation containing polylactic acid, nitrocellulose, an organic pigment, a gelling agent, and a non-aromatic organic solvent.

CITATION LIST

Patent Literature

PTL 1: JP2002-97359A
PTL 2: JP2002-121288A
PTL 3: JP2011-168552A

SUMMARY OF INVENTION

Technical Problem

PTL 2 discloses a polylactic-acid-containing aqueous dispersion. The polylactic-acid-containing aqueous dispersion disclosed in PTL 2, however, as described in Comparative Examples later, cannot form a transparent film at room temperature. Because of the essential components nitrocellulose and an organic solvent, the manicure preparation disclosed in PTL 3 raises concerns about inflammability, solvent odor, effects on human health, and in particular, direct impact on nails caused by the organic solvent. Given these circumstances, an object here is to provide a polylactic-acid-containing aqueous dispersion capable of forming a transparent film at room temperature.

Solution to Problem

The inventors conducted extensive research on formulations capable of forming a transparent film at room temperature, and found that the use of a specific dicarboxylic acid ester as a plasticizer can provide such formulations. They conducted further research, made modifications based on the findings, and provide an invention represented by the following.

Item 1.
A polylactic-acid-containing aqueous dispersion comprising
(1) a polylactic acid,
(2) at least one plasticizer selected from the group consisting of dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof,
(3) at least one dispersion stabilizer selected from the group consisting of cationic polymers, anionic polymers, polyvinyl alcohols, and non-ionic surfactants, and
(4) water.

Item 2.
The polylactic-acid-containing aqueous dispersion according to Item 1, wherein the polylactic acid satisfies at least one of the following physical properties (A) to (D):
(A) 80 to 100 mol % of the total monomer molecules forming the polylactic acid are a lactic acid monomer;
(B) the molar ratio of L-lactic acid to D-lactic acid that form the polylactic acid (L-lactic acid/D-lactic acid) is in the range of 1 to 9;
(C) the reduced viscosity is 0.3 to 1.5 dl/g; and
(D) the number average molecular weight is 10,000 to 90,000.

Item 3.
The polylactic-acid-containing aqueous dispersion according to Item 1 or 2, wherein the at least one plasticizer is present in an amount of 3 to 40 parts by weight per 100 parts by weight of the polylactic acid.

Item 4.
A cosmetic material comprising the polylactic-acid-containing aqueous dispersion according to any one of Items 1 to 3.

Item 5.
The cosmetic material according to Item 4, which is a nail polish liquid, a mascara liquid, or an eyeliner liquid.

Item 6.
Use of the polylactic-acid-containing aqueous dispersion according to any one of Items 1 to 3 as a cosmetic material.

Item 7.
The use according to Item 6, wherein the cosmetic material is a nail polish liquid, a mascara liquid, or an eyeliner liquid.

Item 8.
A method comprising applying the polylactic-acid-containing aqueous dispersion according to any one of Items 1 to 3 to a nail or an eyelash.

Item. 9
A method for producing a cosmetic material, the method comprising adding an additional component to the polylactic-acid-containing aqueous dispersion according to any one of Items 1 to 3.

Item 10.
The method according to Item 9, wherein the cosmetic material is a nail polish liquid, a mascara liquid, or an eyeliner liquid.

Advantageous Effects of Invention

A polylactic-acid-containing aqueous dispersion capable of forming a transparent film at room temperature is provided. The polylactic-acid-containing aqueous dispersion and the film formed from the dispersion are excellent in biodegradability and/or carbon neutrality. The polylactic-acid-containing aqueous dispersion provides a variety of environmentally friendly products (e.g., cosmetic materials).

DESCRIPTION OF EMBODIMENTS

The polylactic-acid-containing aqueous dispersion preferably comprises the following elements (1) to (4):
(1) polylactic acid;
(2) at least one plasticizer selected from the group consisting of dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof;
(3) at least one dispersion stabilizer selected from the group consisting of cationic polymers, anionic polymers, polyvinyl alcohols, and non-ionic surfactants; and
(4) water.

Preferably, the polylactic acid is stably dispersed in water in the presence of a dispersion stabilizer and a plasticizer, and the thus-obtained dispersion is capable of forming a transparent film at room temperature. From this standpoint and to impart excellent biodegradability to the film, in an embodiment, the lower limit of the percentage of the lactic acid monomer of the total monomer molecules forming the polylactic acid is, for example, 80 mol % or more, preferably 90 mol % or more, and more preferably 95 mol % or more, with the upper limit being 100 mol %.

The percentage of the lactic acid monomer of the total monomers forming the polylactic acid (molar ratio) is determined as follows. Polylactic acid is dissolved in deuterated chloroform or deuterated dimethyl sulfoxide, and the dissolved polylactic acid is subjected to 1H-NMR analysis and 13C-NMR analysis using a 400-MR NMR spectrometer (Varian). The composition is determined from the obtained integral ratio. The percentage of the lactic acid monomer (molar ratio) is calculated from the obtained composition.

The lactic acid monomer forming the polylactic acid may be either L-lactic acid or D-lactic acid. However, for the same reasons as above, the upper limit of the molar ratio of L-lactic acid to D-lactic acid (L-lactic acid/D-lactic acid) in the total lactic acid monomers forming the polylactic acid is, for example, 9 or less, preferably 7 or less, and more preferably 5 or less, and the lower limit is 1.

The molar ratio of L-lactic acid to D-lactic acid (L/D) that form the polylactic acid is measured as follows. Polylactic acid is added to a mixture solvent of pure water, 1N sodium hydroxide, and isopropyl alcohol, and heated at 70° C. with stirring for hydrolysis. The resultant is filtered, and the solids in the filtrate are removed, followed by adding sulfuric acid for neutralization, thereby obtaining an aqueous solution containing L-lactic acid and D-lactic acid. The amount of L-lactic acid and D-lactic acid is measured with this aqueous solution as a sample by high-performance liquid chromatography (HPLC) using a chiral ligand exchange column (Sumichiral OA-5000, Sumika Chemical Analysis Service, Ltd.). The molar ratio (L-lactic acid/D-lactic acid) is calculated from the ratio of the peak area assigned to L-lactic acid to the peak area assigned to D-lactic acid.

The lactic acid monomer forming the polylactic acid is also called a "repeating unit" and has the structure represented by the following formula 1.

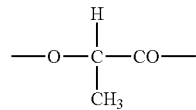

Formula 1

The polylactic acid may contain a monomer molecule other than the lactic acid monomer. Such a monomer molecule is not particularly limited. Examples include caprolactone, hydroxy acid, such as glycolic acid, 2-hydroxyisobutyric acid, 3-hydroxybutyric acid, 4-hydroxybutyric acid, 16-hydroxyhexadecanoic acid, 2-hydroxy-2-methylbutyric acid, 10-hydroxystearic acid, malic acid, citric acid, and gluconic acid, succinic acid, propylene glycol, and glycerine. These may be used singly or in any combination of two or more.

The reduced viscosity ($\eta$SP/C) of the polylactic acid is not particularly limited, and, for example, the lower limit is 0.3 dl/g or more, and preferably 0.4 dl/g or more. The upper limit of the reduced viscosity ($\eta$SP/C) of the polylactic acid is, for example, 1.5 dl/g or less, preferably 1.3 dl/g or less, and still more preferably 1.2 dl/g or less. The reduced viscosity of the polylactic acid can be adjusted by changing the conditions for polymerization reaction, such as polymerization time, polymerization temperature, and degree of depressurization, and by changing the amount of an alcohol component for use as a copolymer component. The reduced viscosity of the polylactic acid is measured at 30° C. using an Ubbelohde viscosity tube by dissolving 0.1 g of the polylactic acid in 25 ml of a mixture solvent of phenol/tetrachloroethane (mass ratio: 6/4).

The lower limit of the glass-transition temperature (Tg) of the polylactic acid is preferably 20° C. or more, preferably 25° C. or more, preferably 30° C. or more, and preferably 35° C. or more, from the standpoint of forming a transparent film at room temperature. The upper limit of Tg is preferably 60° C. or less, preferably 55° C. or less, preferably 53° C. or less, and preferably 50° C. or less. The Tg or the polylactic acid can be adjusted, for example, by changing the proportion of the copolymer component. The Tg of the polylactic acid is a value measured by differential scanning calorimetry (DSC).

The number average molecular weight of the polylactic acid is not particularly limited. From the standpoint of transparent film formation at room temperature, however, the lower limit is preferably 10,000, and more preferably 30,000. The upper limit of the number average molecular weight of the polylactic acid is preferably 90,000, and more preferably 70,000. A number average molecular weight within these ranges allows the polylactic acid to be present in the form of particles with a suitable particle size in a dispersion, which appears to contribute to excellent transparent film formation.

The number average molecular weight of the polylactic acid is measured in accordance with the following procedure. Polylactic acid is dissolved in tetrahydrofuran to give a concentration of about 0.5 mass %, and this solution is filtered through a polytetrafluoroethylene membrane filter with a pore diameter of 0.5 μm. The number average molecular weight of the filtered polylactic acid is measured at 30° C. by gel permeation chromatography (GPC) with an Alliance GPC System (Waters Corporation). A polystyrene standard is used as a molecular weight standard sample.

The polylactic acid that satisfies the physical properties described above is known and can be produced, for example, by the method disclosed in PTL 1. Synthesis methods include a method in which lactide, which is a dimer of lactic acid, is melt-mixed with a monomer molecule other than lactic acid, and the mixture is subjected to ring-opening polymerization with heating using a known ring-opening polymerization catalyst (e.g., tin octylate and aluminium acetylacetonate) and a method in which dehydration-polycondensation is directly performed with heating and depressurization. The polylactic acid can also be synthesized using only lactide, which is a dimer of lactic acid.

The proportion of the polylactic acid in the polylactic-acid-containing aqueous dispersion is not particularly limited as long as a transparent film can be formed at room temperature. The lower limit is, for example, 30%, and preferably 35% on a weight basis, and the upper limit is 70%, and preferably 60%.

The polylactic-acid-containing aqueous dispersion preferably contains a plasticizer so that a transparent film can be formed at room temperature. The plasticizer is preferably at least one member selected from the group consisting of dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, diisopropyl sebacate, and any mixtures thereof. These are all commercially available. The plasticizer is more preferably at least one member selected from the group consisting of dimethyl adipate, diisopropyl adipate, dibutyl adipate, dimethyl succinate, dimethyl glutarate, diethyl sebacate, diisopropyl sebacate, and any mixtures thereof.

The proportion of the plasticizer in the polylactic-acid-containing aqueous dispersion is not particularly limited as long as a transparent film can be formed at room temperature. For example, the plasticizer is added in an amount of 40 parts by weight or less, and preferably 30 parts by weight or less, per 100 parts by weight of the polylactic acid. The lower limit of the proportion of the plasticizer is not particularly limited. For example, the lower limit is 3 parts by weight or more, or 5 parts by weight or more, per 100 parts by weight of the polylactic acid.

The polylactic-acid-containing aqueous dispersion preferably contains a dispersion stabilizer so that the polylactic acid is stably dispersed in an aqueous solvent. The dispersion stabilizer is not particularly limited as long as the polylactic acid can be stably dispersed in water. The dispersion stabilizer is preferably at least one member selected from the group consisting of cationic polymers, anionic polymers, polyvinyl alcohols, and non-ionic surfactants. The average molecular weight of a cationic polymer or an anionic polymer is not particularly limited. In an embodiment, the average molecular weight of a cationic polymer or an anionic polymer is, for example, 5000 or more, and preferably 10000 or more.

Examples of cationic polymers for use as a dispersion stabilizer include cationic acrylic monomers, such as dimethylaminoethyl methacrylate, diethylaminoethyl methacrylate, dimethylaminopropyl methacrylate, dimethylaminoethyl acrylate, diethylaminoethyl acrylate, dimethylaminopropyl acrylate, dimethylaminomethyl methacrylamide, dimethylaminoethyl methacrylamide, dimethylaminopropyl methacrylamide, dimethylaminomethyl acrylamide, dimethylaminoethyl acrylamide, and dimethylaminopropyl acrylamide; and homopolymers and copolymers, such as quaternary ammonium salts, including dimethylaminoethyl methacrylate methyl chloride salts, diethylaminoethyl methacrylate dimethyl sulfuric acid salts, and dimethylaminopropyl methacrylate chloroacetic acid salts, which are obtained by reacting these cationic acrylic monomers with, for example, halogenated alkyl, dialkyl sulfuric acid, or monochloroacetic acid. Examples also include, in addition to the cationic acrylic monomers listed above, acrylic monomers, such as acrylic acid alkyl ester, acrylic acid hydroxy alkyl ester, acrylic acid polyoxyethylene ester, acrylic acid alkoxy polyoxyethylene ester, methacrylic acid alkyl ester, methacrylic acid hydroxy alkyl ester, methacrylic acid polyoxyethylene ester, methacrylic acid alkoxy polyoxyethylene ester, acrylamide, methacrylamide, dimethylacrylamide, diethylacrylamide, isopropylacrylamide, dimethylmethacrylamide, diethylmethacrylamide, methylolacrylamide, and morpholylacrylamide; vinyl ethers, such as ethyl vinyl ether, hydroxybutyl vinyl ether, triethylene glycol vinyl ether, and methoxy triethylene glycol vinyl ether; allyl ethers, such as hydroxyethyl allyl ether, tetraethylene glycol allyl ether, and methoxy ethylene glycol allyl ether; carboxylic acid vinyl esters, such as vinyl acetate, monochlorovinyl acetate, and vinyl pivalate; vinyl amines, such as vinylpyridine, vinylimidazole, and methylvinyl imidazole; diallyl ammonium chloride; and acrylic polymers, such as copolymers of cationic acrylic monomers listed above with a monomer having copolymerizable unsaturated bonds. In an embodiment, the polylactic-acid-containing aqueous dispersion preferably contains at least one member selected from the group consisting of these cationic polymers. In another embodiment, the polylactic-acid-containing aqueous dispersion preferably does not contain at least one member selected from the group consisting of these cationic polymers.

Other cationic polymers usable as a dispersion stabilizer include cyclic imine polymers, such as polyethyleneimine, polypropyleneimine, poly-3-methylpropylimine, and poly-2-ethylpropylimine; unsaturated amine polymers, such as polyvinylamine and polyallylamine; and cationic polymers, such as quaternary ammonium salts thereof. Additionally, polymers formed by adding at least one member selected from the group consisting of alkyl, hydroxy alkyl, acyl, polyoxyalkylene, and carboxy alkyl to these cationic polymers are also usable. Alkyl can be added by reacting alkyl halide with a cationic polymer. Hydroxy alkyl can be added by reacting 1,2-epoxy alkane with a cationic polymer. Acyl can be added by reacting fatty acid or acyl halide with a cationic polymer. Polyoxyalkylene can be added by reacting ethylene oxide with a cationic polymer. Carboxy alkyl can be added by reacting monochloroacetic acid and/or acrylic acid, and the like with a cationic polymer. In an embodiment, the polylactic-acid-containing aqueous dispersion preferably contains at least one member selected from the group consisting of these cationic polymers. In another embodiment, the polylactic-acid-containing aqueous dispersion preferably does not contain at least one member selected from the group consisting of these cationic polymers.

The cationic polymers may be those crosslinked with the following: diprotic acid, such as oxalic acid, malonic acid, succinic acid, glutaric acid, adipic acid, pimelic acid, suberic acid, azelaic acid, and sebacic acid; alkyl esters of these diprotic acids; disocyanates, such as hexamethylene diisocyanate glycidyl ether and diphenylmethane diisocyanate; diepoxys, such as ethylene glycol diglycidyl ether, polyethylene glycol diglycidyl ether, and orthophthalic acid diglycidyl ether; polyglycidyl ethers, such as sorbitan polyglycidyl ether and trimethylolpropane polyglycidyl ether; urea; guanidines; dibasic acid dihalides; and dialdehyde.

When a cationic polymer is a copolymer of a cationic acrylic monomer with another monomer, the content of the cationic acrylic monomer in the monomer molecules forming the cationic polymer is preferably 30 mol % or more.

In an embodiment, a cationic polymer is preferably at least one member selected from the group consisting of (styrene/acrylates/ammonium methacrylate) copolymers, (ethylene diamine/stearyl dimer dilinoleate) copolymers, alkyl acrylate copolymer-ammonium, (acrylates/ethylhexyl acrylate) copolymers, acrylates copolymer-ammonium, (diethylaminoethyl methacrylate/HEMA/perfluoxohexyl ethyl methacrylate) crosspolymers, alkyl acrylate copolymer-ammonium, (allyl stearate/VA) copolymers, and any combinations thereof.

Typically, the cationic polymers are preferably used in the form of a salt of a suitable acid compound. The acid compound includes inorganic acids, such as hydrochloric acid, sulfuric acid, formic acid, and phosphoric acid; and organic acids, such as acetic acid, oxalic acid, tartaric acid, malic acid, benzoic acid, and lactic acid. At least one member selected from the group consisting of these acid compounds and any combinations of these acid compounds can be used. From the standpoint of safety, price, thermal stability, colorability, etc., the acid compound is preferably at least one member selected from the group consisting of acetic acid, phosphoric acid, lactic acid, and combinations thereof.

In an embodiment, a preferable cationic polymer is a polymer containing, as a unit component of the main monomer, at least one member selected from the group consisting of acrylamide, dimethylaminoethyl methacrylate, and monomers such as neutralized products thereof, and quaternary salts of these monomers.

Examples of anionic polymers usable as a dispersion stabilizer include homopolymers formed from monomers selected from the group consisting of unsaturated monocarboxylic acid monomers, unsaturated dicarboxylic acid monomers, and unsaturated sulfonic acid monomers; copolymers formed from any combination of these monomers; and copolymers of these monomers with other copolymerizable monomers (hereinafter, simply referred to as "other monomers"). The unsaturated monocarboxylic acid monomers include acrylic acid, methacrylic acid, crotonic acid, neutralized products of these acids, and partially neutralized products of these acids. The unsaturated dicarboxylic acid monomers include maleic acid, fumaric acid, itaconic acid, citraconic acid, neutralized products of these acids, and partially neutralized products of these acids. The unsaturated sulfonic acid monomers include vinylsulfonic acid, allylsulfonic acid, methacrylic sulfonic acid, styrene sulfonic acid, 2-acrylamide-2-methylpropane sulfonic acid, sulfoethyl (meth)acrylate, sulfoethyl maleimide, 3-allyloxy-2-hydroxypropane sulfonic acid, neutralized products of these acids, and partially neutralized products of these acids. In an embodiment, the polylactic-acid-containing aqueous dispersion preferably contains at least one member selected from the group consisting of these anionic polymers. In another embodiment, the polylactic-acid-containing aqueous dispersion preferably does not contain at least one member selected from the group consisting of these anionic polymers.

The other monomers are not particularly limited, and examples include amide monomers, such as (meth)acrylamide, isopropylamide, and t-butyl (meth)acrylamide; hydrophobic monomers, such as (meth)acrylic acid alkyl ester, styrene, 2-methyl styrene, and vinyl acetate; hydroxy-containing monomers, such as 2-hydroxyethyl (meth)acrylate, polyethylene glycol mono(meth)acrylate, polypropylene glycol mono(meth)acrylate, allyl alcohol, polyethylene glycol monoallyl ether, polypropylene glycol monoallyl ether, 3-methyl-3-buten-1-ol (isoprenol), polyethylene glycol monoisoprenol ether, polypropylene glycol monoisoprenol ether, 3-methyl-2-buten-1-ol (prenol), polyethylene glycol monoprenol ester, polypropylene glycol monoprenol ester, 2-methyl-3-buten-2-ol (isoprene alcohol), polyethylene glycol monoisoprene alcohol ether, polypropylene glycol monoisoprene alcohol ether, N-methylol (meth)acrylamide, glycerol monoallyl ether, and vinyl alcohol; phosphorus-containing monomers, such as (meth)acrylamide methanephosphonic acid, (meth)acrylamide methanephosphonic acid methyl ester, and 2-(meth)acrylamide-2-methyl propane phosphonic acid; methoxy polyethylene glycol (meth)acrylate; and ethoxy propylene glycol (meth)acrylate.

The anionic polymers may be those crosslinked with the following: diprotic acids, such as oxalic acid, malonic acid, succinic acid, glutaric acid, adipic acid, pimelic acid, suberic acid, azelaic acid, and sebacic acid; alkyl esters of these diprotic acids; disocyanates, such as hexamethylene diisocyanate glycidyl ether, and diphenylmethane diisocyanate; diepoxys, such as ethylene glycol diglycidyl ether, polyethylene glycol diglycidyl ether, and orthophthalic acid diglycidyl ether; polyglycidyl ethers, such as sorbitan polyglycidyl ether, and trimethylolpropane polyglycidyl ether; urea; guanidines; dibasic acid dihalides; and dialdehyde.

Typically, the anionic polymers are preferably used in the form of a salt of a suitable basic compound. The basic compound includes hydroxides of alkali metals, hydroxides of alkali earth metals, amine compounds, such as monoethanolamine and diisopropanolamine, and ammonia. At least one member selected from the group consisting of these acid compounds and any combinations of these acid compounds can be used.

In an embodiment, a preferable anionic polymer is a polymer containing methacrylic acid or its neutralized product as a unit component of the main monomer.

The polyvinyl alcohols for use as a dispersion stabilizer are not particularly limited, but the saponification is preferably 70 to 90 mol %, and the average molecular weight is preferably 50000 to 300000.

The non-ionic surfactants for use as a dispersion stabilizer include glycerin fatty acid ester, polyglycerine fatty acid ester, propylene glycol fatty acid ester, polyethylene glycol fatty acid ester, polyoxyethylene fatty acid ester, polyoxyethylene glycol fatty acid ester, polyoxyethylene glycerin fatty acid ester, sorbitan fatty acid ester, sucrose fatty acid ester, polyoxyethylene sorbitan fatty acid ester, polyoxyethylene sorbit fatty acid ester, polyoxyethylene hydrogenated castor oil, alkyl polyglucoside, polyoxyethylene alkyl ether, polyoxyethylene dialkyl ether, polyoxyethylene alkyl allyl ether, polyoxypropylene glyceryl ether, polyoxyethylene polyoxypropylene alkyl ether, polyoxyalkylene alkyl ether, polyoxyethylene glycol, and polyoxyethylene polyoxypropylene glycol. In an embodiment, the polylactic-acid-containing aqueous dispersion preferably contains at least one member selected from the group consisting of these non-ionic surfactants.

The dispersion stabilizers described above may be used singly or in any combination of two or more, as long as the stabilizers for use enable the polylactic acid to stably disperse in water. In an embodiment, from the standpoint of more stable dispersion of the polylactic acid, a preferable dispersion stabilizer is a combination of a cationic polymer and/or an anionic polymer with a non-ionic surfactant and/or polyvinyl alcohol.

The proportion of the dispersion stabilizer in the polylactic-acid-containing aqueous dispersion is not particularly limited as long as the dispersion stabilizer enables the polylactic acid to stably disperse in an aqueous solvent. For example, the lower limit of the proportion of the dispersion stabilizer is 0.01 parts by weight or more, and preferably 0.1 parts by weight or more, per 100 parts by weight of the polylactic acid, and the upper limit is 20 parts by weight or less, and preferably 10 parts by weight or less, per 100 parts by weight of the polylactic acid.

The type of water contained in the polylactic-acid-containing aqueous dispersion is not particularly limited, and can be suitably selected according to the intended use of the polylactic-acid-containing aqueous dispersion. For example, the water for use can be suitably selected from tap water and pure water such as reverse osmosis water (RO water), deionized water, distilled water, and purified water.

The amount of the water contained in the polylactic-acid-containing aqueous dispersion, is not particularly limited as long as the polylactic acid can stably disperse in the water and a transparent film can be formed at room temperature. For example, the water accounts for 30 to 70 wt %, and preferably 40 to 60 wt % of the total amount of the aqueous dispersion.

In an embodiment, the polylactic acid dispersed in the polylactic-acid-containing aqueous dispersion is substantially spherical, and the mean particle size is preferably less than 3 μm, preferably less than 2.5 μm, preferably less than 2 μm, preferably less than 1.5 μm, and preferably less than 1.0 μm, from the standpoint of forming a transparent film at room temperature. The lower limit of the mean particle size is not particularly limited, and is, for example, 0.01 μm or more. Dispersed polylactic acid with such a particle size can be obtained by the use of a combination of the aforementioned polylactic acid with preferable physical properties, dispersion stabilizer, and plasticizer.

The mean particle size of the dispersed polylactic acid can be measured with a particle size distribution analyzer (e.g., Horiba, Ltd.: LA-910 particle size distribution analyser) immediately after the production of the aqueous dispersion.

In an embodiment, the viscosity of the polylactic-acid-containing aqueous dispersion is preferably 100 mPa·s or more, and preferably 150 mPa·s or more, from the standpoint of forming a transparent film at room temperature. The upper limit of the viscosity is, for example, 1000 Pa·s or less, preferably 900 Pa·s or less, preferably 800 Pa·s or less, preferably 700 Pa·s or less, preferably 600 Pa·s or less, preferably 500 mPa·s or less, preferably 450 mPa·s or less, and preferably 400 mPa·s or less. The viscosity can be measured with a B-type viscometer.

In an embodiment, the polylactic-acid-containing aqueous dispersion preferably has properties suitable for cosmetic materials (e.g., nail polish, mascara, and eyeliner). For example, when applied to a nail, the polylactic-acid-containing aqueous dispersion preferably can form a transparent and lustrous film at room temperature within 3 minutes (preferably within 2 minutes). The thus-formed film on a nail preferably can be simply washed off with water (warm or cold) without using a polish remover etc.

The polylactic-acid-containing aqueous dispersion can further contain optional components according to the intended use. For example, the polylactic-acid-containing aqueous dispersion can contain a thickener, a surface smoother, a flow control agent, and the like. The thickener includes polyalkoxide polymers, such as polyethylene glycol; cellulose derivatives, such as methylcellulose, carboxy methylcellulose, hydroxyethyl cellulose, hydroxyethyl methylcellulose, and hydroxypropyl methylcellulose; starch derivatives, such as cationized starch and etherified starch; gums, such as gum arabic, guar gum, and xanthan gum; and animal polymers, such as casein, chitosan, and chitin. The surface smoother includes wax, such as natural wax and synthetic wax. The natural wax includes plant-based natural wax, such as candelilla wax, carnauba wax, rice bran wax, and sumac wax; animal-based natural wax, such as beeswax, lanolin, and spermaceti; mineral-based natural wax, such as montan wax, ozokerite, and ceresin; and petroleum-based natural wax, such as paraffin wax, microcrystalline wax, and petrolatum wax. The synthetic wax includes synthesized hydrocarbons, such as Fischer-Tropsch wax and polyethylene wax; modified wax, such as montan wax derivatives, paraffin wax derivatives, and microcrystalline wax derivatives; hydrogenated wax, such as hydrogenated castor oil and hydrogenated castor oil derivatives; 12-hydroxy stearic acid; stearic acid amide; and anhydrous phthalic imide. In an embodiment, the polylactic-acid-containing aqueous dispersion preferably contains at least one member selected from the group consisting of these components. In another embodiment, the polylactic-acid-containing aqueous dispersion preferably does not contain at least one member selected from the group consisting of these components.

The polylactic-acid-containing aqueous dispersion can be applied to any use in which formation of a transparent film at room temperature is desired. In a preferable embodiment, the polylactic-acid-containing aqueous dispersion is used as a cosmetic material. The type of the cosmetic material is not particularly limited, but is preferably, nail polish, mascara, and eyeliner. The cosmetic material may consist of only the polylactic-acid-containing aqueous dispersion, and can also be obtained by combining the polylactic-acid-containing aqueous dispersion with other component(s). When the aqueous dispersion is combined with the other component(s), the lower limit of the amount of the aqueous dispersion in the cosmetic material is, for example, 1%, and preferably 10%, while the upper limit is 90%, and preferably 80% of the total amount of the cosmetic material. In an embodiment, the polylactic-acid-containing aqueous dispersion preferably does not substantially contain an organic solvent. "Does not substantially contain" means, for example, that the organic solvent used in the process of producing the polylactic acid or the polylactic-acid-containing aqueous dispersion is allowed to remain as a residue in an inevitable amount (e.g., ppm level on a weight basis). In an embodiment (e.g., in the form of nail polish), the polylactic-acid-containing aqueous dispersion may contain at least one organic solvent selected from the group consisting of ethyl acetate, butyl acetate, methyl ethyl ketone, acetone, toluene, n-butanol, and isododecane. In another embodiment, the polylactic-acid-containing aqueous dispersion preferably does not substantially contain at least one member selected from the group consisting of ethyl acetate, butyl acetate, methyl ethyl ketone, acetone, toluene, n-butanol, and isododecane.

In addition to the component(s) described above, the cosmetic material may suitably contain additive(s) typically used in cosmetic materials according to the type of cosmetic material. Examples of additives include powders, such as inorganic powders, organic powders, organic pigments, and pearl pigments; oil components, such as fat and oil, wax, hydrocarbons, silicones, fatty acid esters, higher alcohols, and higher fatty acids; various surfactants, such as non-ionic surfactants, anionic surfactants, cationic surfactants, and ampholytic surfactants; alcohols, such as lower alcohols, polyhydric alcohols, sugar, and sterols; thickeners; ultraviolet absorbers; antioxidants; sequestrants; preservatives; plant and animal extracts, and acids and alkalis. In an embodiment, the polylactic-acid-containing aqueous dispersion preferably contains at least one member selected from the group consisting of these additives. In another embodiment, the polylactic-acid-containing aqueous dispersion preferably does not contain at least one member selected from the group consisting of these additives.

Examples of inorganic powders include talc, kaolin, mica, sericite, calcium carbonate, magnesium carbonate, silicic anhydride, barium sulfate, titanium oxide, zinc oxide, boron nitride, hydroxyapatite, colcothar, yellow iron oxide, black iron oxide, ultramarine, ultramarine pink, ferric hexacyanoferrate, chromium oxide, cobalt oxide, carbon black, and alumina. In an embodiment, the polylactic-acid-containing aqueous dispersion preferably contains at least one member selected from the group consisting of these inorganic powders. In another embodiment, the polylactic-acid-containing aqueous dispersion preferably does not contain at least one member selected from the group consisting of these inorganic powders.

Examples of organic powders include polyamide powder, polyester powder, polyethylene powder, polypropylene powder, silicone powder, polystyrene powder, polyurethane powder, cellulose, silk powder, nylon powder, acrylic powder, lauroyl lysine, styrene-acrylic acid copolymers, vinyl resin, urea resin, fluorine resin, acrylic resin, epoxy resin, and silicon resin. In an embodiment, the polylactic-acid-containing aqueous dispersion preferably contains at least one member selected from the group consisting of these organic powders. In another embodiment, the polylactic-acid-containing aqueous dispersion preferably does not contain at least one member selected from the group consisting of these organic powders.

Examples of organic pigments include red No. 2, red No. 3, red No. 102, red No. 104, red No. 105, red No. 106, red No. 201, red No. 202, red No. 213, red No. 214, red No. 215, red No. 218, red No. 223, red No. 226, red No. 227, red No. 230, red No. 231, red No. 232, red No. 401, red No. 404, red No. 405, red No. 501, red No. 502, red No. 503, red No. 504, red No. 505, red No. 506, yellow No. 4, yellow No. 5, yellow No. 201, yellow No. 202, yellow No. 203, yellow No. 204, yellow No. 402, yellow No. 403, yellow No. 404, yellow No. 405, yellow No. 406, yellow No. 407, green No. 3, green No. 201, green No. 202, green No. 204, green No. 205, green No. 402, blue No. 1, blue No. 2, blue No. 201, blue No. 204, blue No. 205, blue No. 403, orange No. 201, orange No. 203, orange No. 204, orange No. 205, orange No. 206, orange No. 207, orange No. 401, orange No. 402, orange No. 403, purple No. 201, purple No. 401, and black No. 401. The organic pigments may be lake pigments, such as aluminum dye, as well as dyes such as acidic dyes and basic dyes described above. In an embodiment, the polylactic-acid-containing aqueous dispersion preferably contains at least one member selected from the group consisting of these organic pigments. In another embodiment, the polylactic-acid-containing aqueous dispersion preferably does not contain at least one member selected from the group consisting of these organic pigments.

Examples of pearl pigments include titanium mica, mica coated with colcothar, titanium mica coated with colcothar, silica coated with titanium oxide, (PET/polyolefin) laminates, (PET/Al/epoxy resin) laminates, and borosilicic acid (Ca/Na). In an embodiment, the polylactic-acid-containing aqueous dispersion preferably contains at least one member selected from the group consisting of these pearl pigments. In another embodiment, the polylactic-acid-containing aqueous dispersion preferably does not contain at least one member selected from the group consisting of these pearl pigments.

Examples of oil components include fat and oil, such as olive oil, camellia oil, macadamia nut oil, and avocado oil; wax, such as carnauba wax, candelilla wax, jojoba oil, bees wax, and lanolin; hydrocarbons, such as liquid paraffin, paraffin, Vaseline, ceresin, microcrystalline wax, squalene, and squalane; silicones, such as methylpolysiloxane, methylphenylpolysiloxane, methylcyclopolysiloxane, octamethylcyclotetrasiloxane, octamethylcyclopentasiloxane, decamethylcyclopentasiloxane, and methylhydrogenpolysiloxane; fatty acid esters, such as isopropyl myristate, 2-octyldodecyl myristate, cetyl 2-ethylhexanoate, 2-ethylhexyl palmitate, neopentyl glycol di-2-ethylhexanoate, glyceryl tri-2-ethylhexanoate, 2-octyldodecyl oleate, glyceryl triisostearate, glyceryl tri-2-ethylhexanoate, 2-octyldodecyl oleate, diisostearyl malate, glyceryl triisostearate, and diglyceride 2-ethylhexanoate; higher alcohols, such as cetyl alcohol, stearyl alcohol, isostearyl alcohol, 2-octyl dodecanol, and oleyl alcohol; and higher fatty acids, such as lauric acid, myristic acid, palmitic acid, stearic acid, isostearic acid, and oleic acid. In an embodiment, the polylactic-acid-containing aqueous dispersion preferably contains at least one member selected from the group consisting of these oil components. In another embodiment, the polylactic-acid-containing aqueous dispersion preferably does not contain at least one member selected from the group consisting of these oil components.

Examples of surfactants include non-ionic surfactants, such as sorbitan fatty acid ester, glycerin fatty acid ester, castor oil, hydrogenated castor oil, alkylene oxide adducts thereof, polyglycerine fatty acid ester, polyoxyalkylene alkyl ether, polyoxyalkylene fatty acid ester, polyoxyalkylene alkyl phenol, polyoxyethylene sorbit fatty acid ester, polyoxyethylene alkyl phenyl formaldehyde condensates, polyoxyethylene sterol and derivatives thereof, polyoxyethylene lanolin and derivatives thereof, polyoxyethylene bees wax derivatives, and sugar esters; anionic surfactants, such as higher fatty acid soap, alkyl sulfuric acid ester salts, alkyl phosphoric acid salts, polyoxyethylene alkyl ether sulfuric acid salts, polyoxyethylene alkyl phenyl ether sulfuric acid salts, alkyl ether phosphoric esters, alkyl ether carboxylic acid salts, acyl methyl taurine salts, N-acyl-N-methyl-β-alanine salts, N-acyl glycine salts, N-acyl glutamic acid salts, polyoxyethylene alkyl carboxylic acid salts, alkyl phenyl ether sulfonic acid salts, N-acyl sarcosine and salts thereof, and polyoxyethylene palm oil fatty acid monoethanol amide sulfuric acid salts; cationic surfactants, such as amine salts including alkyl amine salts, fatty acid amide amine salts, and ester-containing tertiary amine salts, alkyl quaternary ammonium salts including monoalkyl quaternary ammonium salts, dialkyl quaternary ammonium salts, trialkyl quaternary ammonium salts, and benzalkonium quaternary ammonium salts, cyclic quaternary ammonium salts including alkyl pyridinium salts, and benzethonium chloride; ampholytic surfactants, such as glycine ampholytic surfactants including alkyl glycine salts, carboxy methyl glycine salts, and N-acyl aminoethyl-N-2-hydroxyethyl glycine salts, amino propionic acid ampholytic surfactants including alkyl amino propionic acid salts, and alkyl imino dipropionic acid salts, amino acetic acid betaine ampholytic surfactants including alkyl dimethylamino acetic acid betaine, and fatty acid amide propyl dimethylamino acetic acid betaine, and sulfo betaine ampholytic surfactants including alkyl hydroxy sulfobetaine. In an embodiment, the polylactic-acid-containing aqueous dispersion preferably contains at least one member selected from the group consisting of these surfactants. In another embodiment, the polylactic-acid-containing aqueous dispersion preferably does not contain at least one member selected from the group consisting of these surfactants.

Examples of alcohols include lower alcohols, such as ethanol, isopropanol, and butanol; polyhydric alcohols, such as 1,3-butanediol, glycerine, polyglycerine, ethylene, glycol, propylene glycol, polyethylene glycol, and polypropylene glycol; sugar, such as sorbitol, mannitol, glucose, sucrose, xylitol, lactose, and trehalose; and sterols, such as cholesterol and phytosterol. In an embodiment, the polylactic-acid-containing aqueous dispersion preferably contains at least one member selected from the group consisting of these alcohols. In another embodiment, the polylactic-acid-containing aqueous dispersion preferably does not contain at least one member selected from the group consisting of these alcohols.

Examples of thickeners include, in addition to bentonite and smectite, clay minerals, such as beidellite, nontronite, saponite, hectorite, sauconite, and stevensite; water-soluble polysaccharides, such as carrageenan, guar gum, xanthan gum, gum arabic, gum karaya, gum tragacanth, dextran, amylose, amylopectin, agarose, pullulan, chondroitin sulfate, sodium pectate, alginic acid, methyl cellulose, ethyl cellulose, carboxymethyl cellulose, hydroxyethyl cellulose, and hydroxypropyl cellulose; and vinyl polymers, such as polyvinyl alcohol, and polyvinyl pyrrolidone. In an embodiment, the polylactic-acid-containing aqueous dispersion preferably contains at least one member selected from the group consisting of these thickeners. In another embodiment, the polylactic-acid-containing aqueous dispersion preferably does not contain at least one member selected from the group consisting of these thickeners.

Examples of ultraviolet absorbers include benzoic acid ultraviolet absorbers, such as para-amino benzoic acid, and para-amino benzoic acid monoglycerin ester; anthranilic acid ultraviolet absorbers, such as methyl anthranilate, and homomenthyl-N-acetyl anthranilate; salicylic acid ultraviolet absorbers, such as methyl salicylate; cinnamic acid ultraviolet absorbers, such as octyl p-methoxycinnamate, and ethyl-4-isopropyl cinnamate; benzophenone ultraviolet absorbers, such as 2,4-dihydroxybenzophenone; salicylic acid ultraviolet absorbers, such as amyl salicylate, menthyl salicylate, and benzyl salicylate; and urocanic acid ultraviolet absorbers, such as urocanic acid, and ethyl urocanate. In an embodiment, the polylactic-acid-containing aqueous dispersion preferably contains at least one member selected from the group consisting of these ultraviolet, absorbers. In another embodiment, the polylactic-acid-containing aqueous dispersion preferably does not contain at least one member selected from the group consisting of these ultraviolet absorbers.

Examples of antioxidants include α-tocopherol and derivatives thereof, ascorbic acid and derivatives thereof, erythorbic acid, dibutyl hydroxy toluene, butylhydroxyanisol, gallic acid esters, sulfurous acid, hydrogen sulfite, thiosulfuric acid, thiolactic acid, thioglycolic acid, L-cysteine, and N-acetyl-L-cysteine. In an embodiment, the polylactic-acid-containing aqueous dispersion preferably contains at least one member selected from the group consisting of these antioxidants. In another embodiment, the polylactic-acid-containing aqueous dispersion preferably does not contain at least one member selected from the group consisting of these antioxidants.

Examples of sequestrants include edetate, phosphoric acid, sodium polyphosphate, sodium metaphosphate, alanine, sodium oxalate, nitrilotriacetic acid, 1,2-diaminocyclohexane-tetraacetic acid, N-oxyethylethylene diamine-triacetic acid, ethylene glycol bis-tetraacetic acid, ethylene diamine tetrapropionic acid, 1-hydroxyhexane-1,1-diphosphonic acid, phosphonoacetic acid, diethylenetriamine pentaacetic acid, 1,2-cyclohexanediamine tetraacetic acid, ethylenediamine diacetic acid, and triethylenetetramine hexaacetic acid. In an embodiment, the polylactic-acid-containing aqueous dispersion preferably contains at least one member selected from the group consisting of these sequestrants. In another embodiment, the polylactic-acid-containing aqueous dispersion preferably does not contain at least one member selected from the group consisting of these sequestrants.

Examples of preservatives include parabens, such as methylparaben, ethylparaben, and butylparaben, phenols, such as isopropyl methylphenol, chlorhexidine gluconate solutions, trichlorocarbanilide, phenoxyethanol, carbolic acid, and hexachlorophene, benzoic acid and salts thereof, undecylenic acid, salicylic acid, sorbic acid and salts thereof, dehydroacetic acid and salts thereof, light-sensing element No. 101, light-sensing element No. 201, light-sensing element No. 401, hinokitiol, and triclosan. In an embodiment, the polylactic-acid-containing aqueous dispersion preferably contains at least one member selected from the group consisting of these preservatives. In another embodiment, the polylactic-acid-containing aqueous dispersion preferably does not contain at least one member selected from the group consisting of these preservatives.

In an embodiment, the components contained in the polylactic-acid-containing aqueous dispersion are preferably naturally occurring substances.

EXAMPLES

The following Examples describe the present invention in more detail. However, the present invention is not limited to these Examples.

Production Example 1

Polylactic Acid A 120 g of L-lactide, 80 g of DL-lactide, 0.3 g of ethylene glycol, and 180 mg of acetoacetyl aluminium were added to a flask, and the mixture was subjected to a reaction in a nitrogen atmosphere at 180° C. for 3 hours, followed by removing the lactide monomer by depressurization, thereby preparing polylactic acid A.

Production Example 2

Polylactic Acid B 120 g of L-lactide, 80 g of DL-lactide, 0.1 g of ethylene glycol, and 36 mg of tin octylate were added to a flask, and the mixture was subjected to a reaction in a nitrogen atmosphere at 180° C. for 3 hours, followed by removing the lactide monomer by depressurization, thereby preparing polylactic acid B.

Production Example 3

Polylactic Acid C 120 g of L-lactide, 80 g of DL-lactide, 1.1 g of sodium isethionate, and 36 mg of tin octylate were added to a flask, and the mixture was subjected to a reaction in a nitrogen atmosphere at 180° C. for 3 hours, followed by removing the lactide monomer by depressurization, thereby preparing polylactic acid C.

Production Example 4

Polylactic Acid D 108 g of L-lactide, 72 g of DL-lactide, 20 g of caprolactam, 1.0 g of sorbitol, and 37 mg of tin octylate were added to a flask, and the mixture was subjected to a reaction in a nitrogen atmosphere at 180° C. for 3 hours, followed by removing the lactide monomer by depressurization, thereby preparing polylactic acid D.

Test Example 1

Physical Properties of Polylactic Acids

Polylactic acids A to D were measured for the following: the number average molecular weight, the glass-transition temperature (Tg), the specific gravity, the reduced viscosity, the molar ratio (L/D) of L-lactic acid and D-lactic acid forming the polylactic acid, and the mole fraction of the lactic acid monomer (the proportion of lactic acid) forming the polylactic acid in the total monomers. The measurement methods are as described below. Table 1 below shows the measurement results.

Method for Measuring Number Average Molecular Weight

Each of the polylactic acids was dissolved in tetrahydrofuran to give a concentration of about 0.5 mass %, and each solution was filtered through a polytetrafluoroethylene membrane filter with a pore diameter of 0.5 μm. The number average molecular weight of the filtered polylactic acid was measured at 30° C. by gel permeation chromatography (GPC) with an Alliance GPC System (Waters Corporation). A polystyrene standard was used as a molecular weight standard sample.

Method for Measuring Tg 5 mg of each of the polylactic acids was placed in an aluminum sample pan and hermetically sealed. The temperature was increased from −20° C. to 120° C. at a temperature increase rate of 20° C./min with a DSC-220 differential scanning calorimeter (Seiko Instruments Inc.), and the polylactic acids were cooled at a given rate, followed by increasing the temperature from −20° C. to 120° C. at a temperature increase rate of 10° C./min, thereby determining their DSC curves. The glass-transition temperature (Tg) was determined by the midpoint method.

Method for Measuring Reduced Viscosity 0.1 g of each of the polylactic acids was dissolved in 25 ml of a mixture solvent (phenol/tetrachloroethane, mass ratio 6/4), and the solutions were measured at 30° C. with an Ubbelohde viscosity tube.

Method for Measuring Specific Gravity

An amount of each of the polylactic acids was weighed and measured at 30° C. with an SD-200L electronic hydrometer.

Method for Measuring Molar Ratio (L/D) of D-Lactic Acid to L-Lactic Acid

Each of the polylactic acids was added to a mixture solvent of pure water, 1N sodium hydroxide, and isopropyl alcohol, and heated at 70° C. with stirring to hydrolyze it. Each of the resultants was filtered, and the solids in the filtrate were removed, followed by adding sulfuric acid for neutralization, thereby obtaining an aqueous solution containing L-lactic acid and D-lactic acid. The amounts of L-lactic acid and D-lactic acid of these aqueous solutions as samples were measured by high-performance liquid chromatography (HPLC) using a chiral ligand exchange column (Sumichiral OA-5000, Sumika Chemical Analysis Service, Ltd.). The molar ratio (L-lactic acid/D-lactic acid) was calculated from the ratio of the peak area assigned to L-lactic acid to the peak area assigned to D-lactic acid.

Method for Measuring Mole Fraction of Lactic Acid Monomer in Total Monomers 15 mg of each of the polylactic acids was dissolved in 0.5 mL of deuterated chloroform, and the value of the proton integral was determined with a nuclear magnetic resonance (NMR) spectrometer (400 MHz, Varian). Based on the value, the mole fraction of the lactic acid monomer was determined. Measurement was performed at room temperature with dl=26 s.

TABLE 1

| Polylactic Acid | Mn (×10³) | Tg | Specific Gravity (at 30° C.) | Reduced Viscosity (dl/g) | L/D | Percentage of Lactic Acid (wt %) |
|---|---|---|---|---|---|---|
| A | 30 | 50 | 1.26 | 0.5 | 4 | >99 |
| B | 70 | 50 | 1.26 | 0.8 | 4 | >99 |
| C | 30 | 50 | 1.26 | 0.5 | 4 | >99 |
| D | 30 | 30 | 1.24 | 0.5 | 4 | 90 |

Production Example 5

Polylactic-Acid-Containing Aqueous Dispersion 50 g of polylactic acid A was weighed and dissolved in 100 g of ethyl acetate. 0.3 g of an acrylamide/methacrylic acid copolymer, 15 g of a plasticizer shown in Table 2 below, and 62.5 g of deionized water were added to this solution. The mixture was packed in a high-pressure disperser, heated to 120° C., and stirred at 10,000 rpm for 3 minutes, followed by cooling to 40° C. Subsequently, ethyl acetate was removed by condensation with heating, thereby obtaining an aqueous dispersion in which polylactic acid A was dispersed. The aqueous dispersion containing polylactic acid A had a solids content of 47.4 wt %, a mean particle size of 0.5 μm, a viscosity of 330 mPa·s, and a pH of 2.4.

Test Example 2

Evaluation of Film Formation

The polylactic-acid-A-containing aqueous dispersion obtained in Production Example 5 was applied to a polypropylene plate, and spread with an applicator to give a thickness of 100 μm. The plate was then allowed to stand at 20, 25, 30, 40, or 75° C. After 60 minutes, whether a film was formed and the transparency and luster of the film were evaluated. Table 2 below shows the measurement results.

TABLE 2

| Plasticizer | 20° C. | 25° C. | 30° C. | 40° C. | 75° C. | Transparency | Luster |
|---|---|---|---|---|---|---|---|
| Dimethyl adipate | ○ | ○ | ○ | ○ | ○ | ○ | Yes |
| Diethyl adipate | ○ | ○ | ○ | ○ | ○ | ○ | Yes |
| Dipropyl adipate | ○ | ○ | ○ | ○ | ○ | ○ | Yes |
| Diisopropyl adipate | ○ | ○ | ○ | ○ | ○ | ○ | Yes |
| Dibutyl adipate | ○ | ○ | ○ | ○ | ○ | ○ | Yes |
| Diisobutyl adipate | Δ | Δ | Δ | Δ | Δ | x | No |
| Diallyl adipate | ○ | ○ | ○ | ○ | ○ | ○ | Yes |
| Diheptyl adipate | x | x | x | x | ○ | x | No |
| Diisononyl adipate | x | x | x | x | ○ | x | No |
| Diisodecyl adipate | x | x | x | x | ○ | x | No |
| Di-n-alkyl adipate (mixture) | x | x | x | x | ○ | x | No |
| Adipic acid ester* | x | x | Δ | Δ | Δ | x | No |
| Bis(2-butoxyethyl) adipate | ○ | ○ | ○ | ○ | ○ | ○ | Yes |
| Bis(2-ethylhexyl) adipate | x | x | x | x | ○ | x | No |
| Bis(2-methoxyethyl) adipate | ○ | ○ | ○ | ○ | ○ | ○ | Yes |
| Diisooctadecyl adipate | x | x | x | x | ○ | x | No |
| Dimethyl succinate | ○ | ○ | ○ | ○ | ○ | ○ | Yes |
| Dimethyl glutarate | ○ | ○ | ○ | ○ | ○ | ○ | Yes |
| Diethyl sebacate | ○ | ○ | ○ | ○ | ○ | ○ | Yes |
| Diisopropyl sebacate | ○ | ○ | ○ | ○ | ○ | ○ | Yes |
| Dibutyl sebacate | x | x | x | x | ○ | x | No |
| Diisopropylamine | x | x | x | x | ○ | x | No |
| N,N'-diisopropyl ethylenediamine | x | x | x | x | ○ | x | No |
| Decaglyceryl monostearate | x | x | x | x | ○ | x | No |
| Diglyceryl monostearate | x | x | x | x | ○ | x | No |
| Triglyceryl monostearate | x | x | x | x | ○ | x | No |

In Table 2, the symbol "○" indicates that a transparent film was formed. The symbol "Δ" indicates that a somewhat transparent white film was formed. The symbol "x" indicates that an opaque, stark white film was formed. Interestingly, a transparent film was formed at room temperature only when dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, or diisopropyl sebacate was used. A white paper sheet with black letters written on it (font size: 14 pt) was laid under the polypropylene plate on which the film was formed, and when the letters were clearly recognized, the film was determined to be transparent. When the film was found to be glossy, the film was determined to be lustrous. In Table 2, the symbol "*" indicates a commercially available Daifatty-101 plasticizer (Daihachi Chemical Industry Co., Ltd.), which is usable for polylactic acid.

Test Example 3

Evaluation of Film Formation

An aqueous dispersion in which polylactic acid A was dispersed was prepared in the same manner as in Production Example 5, except that a dimethylaminoethyl methacrylate acrylamide copolymer was used instead of the acrylamide/methacrylic acid copolymer. The obtained polylactic-acid-A-containing aqueous dispersion had a solids content of 48.9 wt %, a mean particle size of 0.5 μm, a viscosity of 398 mPa·s, and a pH of 2.6. The film formation of the obtained polylactic-acid-A-containing aqueous dispersion was evaluated in the same manner as in Test Example 2. Table 3 below shows the results.

TABLE 3

| Plasticizer | 20° C. | 25° C. | 30° C. | 40° C. | 75° C. | Transparency | Luster |
|---|---|---|---|---|---|---|---|
| Dimethyl adipate | ○ | ○ | ○ | ○ | ○ | ○ | Yes |
| Diethyl adipate | ○ | ○ | ○ | ○ | ○ | ○ | Yes |
| Dipropyl adipate | ○ | ○ | ○ | ○ | ○ | ○ | Yes |
| Diisopropyl adipate | ○ | ○ | ○ | ○ | ○ | ○ | Yes |
| Dibutyl adipate | ○ | ○ | ○ | ○ | ○ | ○ | Yes |
| Diisobutyl adipate | Δ | Δ | Δ | Δ | Δ | x | No |
| Diallyl adipate | ○ | ○ | ○ | ○ | ○ | ○ | Yes |
| Diheptyl adipate | x | x | x | x | ○ | x | No |
| Diisononyl adipate | x | x | x | x | ○ | x | No |
| Diisodecyl adipate | x | x | x | x | ○ | x | No |
| Di-n-alkyl adipate (mixture) | x | x | x | x | ○ | x | No |
| Adipic acid ester* | x | x | Δ | Δ | Δ | x | No |
| Bis(2-butoxyethyl) adipate | ○ | ○ | ○ | ○ | ○ | ○ | Yes |
| Bis(2-ethylhexyl) adipate | x | x | x | x | ○ | x | No |
| Bis(2-methoxyethyl) adipate | ○ | ○ | ○ | ○ | ○ | ○ | Yes |
| Diisooctadecyl adipate | x | x | x | x | ○ | x | No |
| Dimethyl succinate | ○ | ○ | ○ | ○ | ○ | ○ | Yes |
| Dimethyl glutarate | ○ | ○ | ○ | ○ | ○ | ○ | Yes |
| Diethyl sebacate | ○ | ○ | ○ | ○ | ○ | ○ | Yes |
| Diisopropyl sebacate | ○ | ○ | ○ | ○ | ○ | ○ | Yes |

TABLE 3-continued

| Plasticizer | 20° C. | 25° C. | 30° C. | 40° C. | 75° C. | Transparency | Luster |
|---|---|---|---|---|---|---|---|
| Dibutyl sebacate | x | x | x | x | ○ | x | No |
| Diisopropylamine | x | x | x | x | ○ | x | No |
| N,N'-diisopropyl ethylenediamine | x | x | x | x | ○ | x | No |
| Decaglyceryl monostearate | x | x | x | x | ○ | x | No |
| Diglyceryl monostearate | x | x | x | x | ○ | x | No |
| Triglyceryl monostearate | x | x | x | x | ○ | x | No |

As described above, the same results as in Test Example 2 were obtained. Specifically, a transparent film was formed at room temperature only when dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, or diisopropyl sebacate was used as a plasticizer.

Test Example 4

Evaluation of Film Formation

An aqueous dispersion in which polylactic acid A was dispersed was prepared in the same manner as in Production Example 5, except that dimethylaminoethyl acrylate/acrylamide/methacrylamide was used instead of the acrylamide/methacrylic acid copolymer. The film formation of the obtained polylactic-acid-A-containing aqueous dispersion was evaluated in the same manner as in Test Example 2. The results were the same as in Test Examples 2 and 3. Specifically, a transparent film was formed at room temperature only when dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl, succinate, dimethyl glutarate, diethyl sebacate, or diisopropyl sebacate was used as a plasticizer.

Test Example 5

Evaluation of Film Formation

An aqueous dispersion in which polylactic acid B was dispersed was prepared in the same manner as in Production Example 5, except that polylactic acid B was used instead of polylactic acid A. The film formation of the obtained polylactic acid B-containing aqueous dispersion was evaluated in the same manner as in Test Example 2. The results were the same as in Test Examples 2 and 3. Specifically, a transparent film was formed at room temperature only when dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, or diisopropyl sebacate was used as a plasticizer.

As described above, the same results as in Test Example 2 were obtained. Specifically, a transparent film was formed at room temperature only when dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, or diisopropyl sebacate were used as a plasticizer. The use of polylactic acid C or D instead of polylactic acid A also yielded the same results.

Test Example 6

Evaluation of Film Formation

An aqueous dispersion in which polylactic acid F or G was dispersed was prepared in the same manner as in Production Example 5, except that polylactic acids that satisfy the physical properties shown in Table 4 below were used instead of polylactic acid A. The film formation of the obtained polylactic acid F- or G-containing aqueous dispersion was evaluated in the same manner as in Test Example 2. The results revealed that when any plasticizer shown in Table 2 was used, no film was formed at room temperature, and white solids, which were the dried dispersion, were formed without producing a transparent film.

TABLE 4

| Polylactic Acid | Mn (×10$^3$) | Tg | Reduced Viscosity (dl/g) | L/D | Percentage of Lactic Acid (wt %) |
|---|---|---|---|---|---|
| F | 120 | 55 | 1.89 | 24 | >99 |
| G | 180 | 57 | 1.23 | 30 | >99 |

Test Example 7

Evaluation of Film Formation on Nail

The polylactic-acid-A-containing aqueous dispersion (dimethyl adipate was used as a plasticizer) obtained in Production Example 5 was applied to the nails of panelists, and allowed to stand for 2 minutes, followed by examining whether films were formed in the same manner as in Test Example 2. The results confirmed the formation of transparent and lustrous films.

Formulation Example 1

Nail Polish

Nail polish of the following formulation was prepared using the polylactic-acid-A-containing aqueous dispersion (dimethyl adipate was used as a plasticizer) obtained in Production Example 5. The proportion of the components is indicated by mass %.

| | |
|---|---|
| (1) Purified Water | 15.1 |
| (2) 1,3-Butylene Glycol | 1.0 |
| (3) Synthetic Hectorite (Note 1) | 0.3 |
| (4) Xanthan Gum | 0.3 |

-continued

| | |
|---|---|
| (5) Preservative | 0.3 |
| (6) Polylactic-acid-A-containing Aqueous Dispersion of Production Example 5 | 80.0 |
| (7) Synthetic Titanium Mica (Note 2) | 3.0 |
| Total | 100.0 |

(Note 1): LAPONITE XLS (Rockwood)
(Note 2): DK PEARL-SY SILVER (Daito Kasei Kogyo Co., Ltd.)

The nail polish was prepared in accordance with the following procedure. Components (1) to (5) were mixed and homogeneously dissolved. Subsequently, component (6) was added, and then component (7) was added. After being mixed well, the mixture was packed in a container, thereby preparing nail polish.

Formulation Example 2

Mascara

Mascara of the following formulation was prepared using the polylactic-acid-A-containing aqueous dispersion (diethyl adipate was used as a plasticizer) of Production Example 5. The proportion of the components is indicated by mass %.

| | |
|---|---|
| (1) Stearic Acid | 4.0 |
| (2) Bees Wax | 5.0 |
| (3) Carnauba Wax | 3.0 |
| (4) Paraffin Wax | 3.0 |
| (5) Purified Water | 39.0 |
| (6) Propylene Glycol | 10.0 |
| (7) Triethanol Amine | 3.5 |
| (8) Black Iron Oxide | 10.0 |
| (9) Polylactic-acid-A-containing Aqueous Dispersion of Production Example 5 | 20.0 |
| (10) Sorbitan Sesquioleate | 2.0 |
| (11) Preservative | 0.5 |
| Total | 100.0 |

The mascara was prepared in accordance with the following procedure. Components (1) to (4) were mixed and homogeneously dissolved with heating, thereby preparing mixture (A). At the same time, components (6), (8), and (10) were homogeneously mixed, thereby preparing mixture (B). Further, components (5), (7), and (11) were mixed and homogeneously dissolved with heating, thereby preparing mixture (C). Mixture (A) was added to mixture (C) to give an emulsion, and mixture (B) was added to the emulsion. This mixture was homogeneously mixed and packed in a suitable container, thereby preparing mascara.

The thus-prepared mascara was used, and the feeling, as well as the finish, were found to be excellent.

Formulation Example 3

Eyeliner

Eyeliner of the following formulation was prepared using the polylactic-acid-A-containing aqueous dispersion (dipropyl adipate was used as a plasticizer) of Production Example 5. The proportion of the components is indicated by mass %.

| | |
|---|---|
| (1) Purified Water | 61.1 |
| (2) 1,3-Butylene Glycol | 1.0 |

-continued

| | |
|---|---|
| (3) Xanthan Gum | 0.7 |
| (4) Synthetic Hectorite (Note 3) | 0.7 |
| (5) Preservative | 0.5 |
| (6) 40% Ferric Hexacyanoferrate Aqueous Dispersion (Note 4) | 12.0 |
| (7) 50% Titanium Oxide Aqueous Dispersion (Note 5) | 4.0 |
| (8) Polylactic-acid-A-containing Aqueous Dispersion of Production Example 5 | 20.0 |
| Total | 100 |

(Note 3): LAPONITE XLS (Rockwood)
(Note 4): WD-FB40 (Daito Kasei Kogyo Co., Ltd.)
(Note 5): WD-Ti50 (Daito Kasei Kogyo Co., Ltd.)

The eyeliner was prepared in accordance with the following procedure. Components (1) to (5) were homogeneously mixed, and components (6) and (7) were added thereto. Subsequently, component (8) was further added. The mixture was homogeneously mixed and packed in an airtight container with a brush attached. The obtained eyeliner was excellent in eyelid adhesion, feeling, and finish.

The invention claimed is:

1. A cosmetic material comprising a polylactic-acid-containing aqueous dispersion comprising
   (1) a polylactic acid,
   (2) at least one plasticizer selected from the group consisting of dimethyl adipate, diethyl adipate, dipropyl adipate, diisopropyl adipate, dibutyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof,
   (3) at least one dispersion stabilizer that is a cationic polymer comprising at least one monomer selected from the group consisting of acrylamide, dimethylaminoethyl methacrylate, a neutralized product of acrylamide, a neutralized product of dimethylaminoethyl methacrylate, a quaternary salt of acrylamide, and a quaternary salt of dimethylaminoethyl methacrylate, and
   (4) water,
   wherein
   the polylactic-acid-containing aqueous dispersion comprises the polylactic acid in a range of 30 to 70 wt %,
   the polylactic-acid-containing aqueous dispersion has a viscosity in a range of 150 mPa·s or more and 400 mPa·s or less, and
   the cosmetic material forms a transparent film at room temperature within three minutes.

2. The cosmetic material according to claim 1, wherein the polylactic acid satisfies at least one of the following physical properties (A) to (D):
   (A) 80 to 100 mol % of the total monomer molecules forming the polylactic acid are a lactic acid monomer;
   (B) the molar ratio of L-lactic acid to D-lactic acid that form the polylactic acid (L-lactic acid/D-lactic acid) is in the range of 1:1 to 7:1;
   (C) when 0.1 g of the polylactic acid is dissolved in 25 mL of a mixture of phenol/tetrachloroethane in a mass ratio of 6/4, and a reduced viscosity is measured at 30° C., the reduced viscosity is 0.3 to 1.5 dl/g; and
   (D) the number average molecular weight is 10,000 to 90,000.

3. The cosmetic material according to claim 2, wherein the polylactic-acid-containing aqueous dispersion comprises the at least one plasticizer in an amount of 3 to 40 parts by weight per 100 parts by weight of the polylactic acid.

4. The cosmetic material according to claim 2, wherein the polylactic acid satisfies the physical property (A).

5. The cosmetic material according to claim 2, wherein the polylactic acid satisfies the physical property (B).

6. The cosmetic material according to claim 2, wherein the polylactic acid satisfies the physical property (C).

7. The cosmetic material according to claim 2, wherein the polylactic acid satisfies the physical property (D).

8. The cosmetic material according to claim 2, wherein the polylactic acid satisfies the physical properties (A) and (B).

9. The cosmetic material according to claim 2, wherein the polylactic acid satisfies the physical properties (A) and (C).

10. The cosmetic material according to claim 2, wherein the polylactic acid satisfies the physical properties (A) and (D).

11. The cosmetic material according to claim 2, wherein the polylactic acid satisfies the physical properties (A), (B), and (C).

12. The cosmetic material according to claim 2, wherein the polylactic acid satisfies the physical properties (A), (B), and (D).

13. The cosmetic material according to claim 2, wherein the polylactic acid satisfies the physical properties (A), (B), (C), and (D).

14. The cosmetic material according to claim 13, wherein the polylactic-acid-containing aqueous dispersion comprises the at least one plasticizer in an amount of 3 to 40 parts by weight per 100 parts by weight of the polylactic acid.

15. The cosmetic material according to claim 14, wherein the at least one plasticizer is selected from the group consisting of diethyl adipate, dipropyl adipate, diisopropyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof.

16. The cosmetic material according to claim 2, wherein the polylactic acid satisfies the physical property (D), wherein the number average molecular weight is 10,000 to 70,000.

17. The cosmetic material according to claim 1, wherein the polylactic-acid-containing aqueous dispersion comprises the at least one plasticizer in an amount of 3 to 40 parts by weight per 100 parts by weight of the polylactic acid.

18. The cosmetic material according to claim 1, wherein the at least one plasticizer is selected from the group consisting of diethyl adipate, dipropyl adipate, diisopropyl adipate, diallyl adipate, bis(2-butoxyethyl) adipate, bis(2-methoxyethyl) adipate, dimethyl succinate, dimethyl glutarate, diethyl sebacate, diisopropyl sebacate, and mixtures thereof.

19. The cosmetic material according to claim 1, wherein the polylactic acid is in the form of particles with a mean particle size of less than 1.0 µm.

* * * * *